(12) United States Patent
Nakata et al.

(10) Patent No.: US 11,058,311 B2
(45) Date of Patent: Jul. 13, 2021

(54) LIVING BODY INFORMATION SENSOR

(71) Applicant: Rohm Co., Ltd., Kyoto (JP)

(72) Inventors: Yuichiro Nakata, Kyoto (JP);
Yoshitsugu Uedaira, Kyoto (JP)

(73) Assignee: Rohm Co., Ltd., Kyoto (JP)

( * ) Notice: Subject to any disclaimer, the term of this patent is extended or adjusted under 35 U.S.C. 154(b) by 670 days.

(21) Appl. No.: 15/575,548

(22) PCT Filed: Apr. 1, 2016

(86) PCT No.: PCT/JP2016/060954
§ 371 (c)(1),
(2) Date: Nov. 20, 2017

(87) PCT Pub. No.: WO2016/185810
PCT Pub. Date: Nov. 24, 2016

(65) Prior Publication Data
US 2018/0125381 A1 May 10, 2018

(30) Foreign Application Priority Data
May 21, 2015 (JP) .............................. JP2015-103685

(51) Int. Cl.
*A61B 5/024* (2006.01)
*A61B 5/00* (2006.01)
*A61B 5/103* (2006.01)

(52) U.S. Cl.
CPC ........ *A61B 5/02444* (2013.01); *A61B 5/0004* (2013.01); *A61B 5/02438* (2013.01);
(Continued)

(58) Field of Classification Search
None
See application file for complete search history.

(56) References Cited

U.S. PATENT DOCUMENTS 5,088,817 A * 2/1992 Igaki ................. G06K 9/00046
250/556
2004/0193063 A1 9/2004 Kimura et al.
(Continued)

FOREIGN PATENT DOCUMENTS

CN 102551686 A 7/2012
CN 104207755 A 12/2014
(Continued)

OTHER PUBLICATIONS

The State Intellectual Property Office of P.R. China; Office Action mailed in counterpart Chinese Application No. 201680029180.3 (dated Oct. 23, 2019) (submitted with English-language translation).
(Continued)

*Primary Examiner* — Pascal M Bui Pho
*Assistant Examiner* — Marjan Saboktakin
(74) *Attorney, Agent, or Firm* — Fish & Richardson P.C.

(57) ABSTRACT

A light emitting unit emits light including first light and second light. A light receiving unit outputs a signal of a level in accordance with intensity of incoming light. A first optical sensor is configured to outputs a first signal of a level in accordance with intensity of the first light entering the light receiving unit. A second optical sensor outputs a second signal of a level in accordance with intensity of the second light entering the light receiving unit. Based on the second signal, a controller determines whether or not the living body information sensor and a surface of the living body are in close contact with each other. The controller generates the information related to the living body based on the first signal obtained when the living body information sensor and the surface of the living body are in close contact with each other.

13 Claims, 9 Drawing Sheets

(52) U.S. Cl.
CPC .......... *A61B 5/1032* (2013.01); *A61B 5/6843* (2013.01); *A61B 5/721* (2013.01); *A61B 5/02405* (2013.01); *A61B 5/02416* (2013.01); *A61B 5/681* (2013.01); *A61B 5/7225* (2013.01); *A61B 5/7257* (2013.01); *A61B 2562/043* (2013.01)

(56) References Cited

U.S. PATENT DOCUMENTS

| | | |
|---|---|---|
| 2012/0150047 A1 | 6/2012 | Terumoto et al. |
| 2014/0180042 A1* | 6/2014 | Addison ............ A61B 5/14551 600/324 |
| 2014/0206965 A1* | 7/2014 | De Haan .............. A61B 5/7207 600/323 |
| 2014/0275852 A1* | 9/2014 | Hong ................. A61B 5/02427 600/301 |
| 2014/0378780 A1 | 12/2014 | Shimazaki et al. |

FOREIGN PATENT DOCUMENTS

| | | |
|---|---|---|
| JP | 2004-261366 | 9/2004 |
| JP | 2012-143316 | 8/2012 |
| JP | 2015-002930 | 1/2015 |
| JP | 5930011 | 5/2016 |
| KR | 1020130043486 A | 4/2013 |

OTHER PUBLICATIONS

Japan Patent Office, International Search Report for PCT/JP2016/060954 dated Jul. 5, 2016 (with English translation).

* cited by examiner

LIVING BODY INFORMATION SENSOR

TECHNICAL FIELD

The present invention relates to a living body information sensor, and particularly to a wearable living body information sensor.

BACKGROUND ART

Wearable living body information sensors have been conventionally known. For example, Japanese Patent Laying-Open No. 2012-143316 (PTD 1) discloses a wearable living body information sensor. The living body information sensor includes first and second optical sensors and an arithmetic circuit. The first optical sensor includes a first light emitting unit emitting light of the first luminescence intensity to a living body, and a first light receiving unit receiving the light emitted from the first light emitting unit and reflected inside the living body to generate a first light receiving signal. The second optical sensor includes a second light emitting unit emitting light of the second luminescence intensity lower than the first luminescence intensity to a living body, and a second light receiving unit receiving the light emitted from the second light emitting unit and reflected inside the living body to generate a second light receiving signal. The arithmetic circuit subtracts the second light receiving signal from the first light receiving signal to obtain pulse wave data.

CITATION LIST

Patent Document

PTD 1: Japanese Patent Laying-Open No. 2012-143316

SUMMARY OF INVENTION

Technical Problem

When the living body information such as a heart rate is measured while a user wearing a living body information sensor is exercising, or when the user wears the living body information sensor in an erroneous manner, a gap may occur between the living body information sensor and the user's body surface. When such a gap occurs, not only the light reflected inside the living body but also the light reflected off the surface of the living body enters the light receiving unit of the living body information sensor. For example, when a heart rate is measured, the reflected light from the inside of the living body is required. Thus, the light reflected off the surface of the living body becomes noise when the heart rate is calculated, which may lead to a deterioration in the accuracy of measurement.

Therefore, a main object of the present invention is to provide a living body information sensor capable of improving the accuracy of measurement.

Solution to Problem

A living body information sensor according to the present invention is configured to be attached to a living body and to generate information related to the living body. The living body information sensor includes a light emitting unit, a light receiving unit, and a controller. The light emitting unit is configured to emit light including first light and second light. The light receiving unit includes a first optical sensor and a second optical sensor, and is configured to output a signal of a level in accordance with intensity of incoming light. The controller is configured to receive a signal output from the light receiving unit to generate the information related to the living body. When the living body information sensor is attached to the living body, light emitted from the light emitting unit is reflected off the living body and enters the light receiving unit. The first optical sensor is configured to output a first signal of a level in accordance with intensity of the first light entering the light receiving unit. The second optical sensor is configured to output a second signal of a level in accordance with intensity of the second light entering the light receiving unit. The controller is configured to determine, based on the second signal, whether or not the living body information sensor and a surface of the living body are in close contact with each other. The controller is configured to generate the information related to the living body based on the first signal obtained when the living body information sensor and the surface of the living body are in close contact with each other.

By the above-described configuration, the information related to the living body can be calculated based on the signal with less noise obtained when the living body information sensor is in close contact with the living body. Consequently, the living body information sensor can improve the accuracy of measurement.

Preferably, when the level of the second signal is smaller than a prescribed threshold value, the controller determines that the living body information sensor and the surface of the living body are in close contact with each other.

Preferably, the light emitted from the light emitting unit further includes third light. The light receiving unit further includes a third optical sensor. The third optical sensor is configured to output a third signal of a level in accordance with intensity of the third light entering the light receiving unit. The controller is configured to generate the information related to the living body based on the first signal and the third signal that are obtained when the living body information sensor and the surface of the living body are in close contact with each other.

Preferably, the controller is configured to generate the information related to the living body based on a difference between the level of the first signal and the level of the third signal.

Preferably, the first light is green light. The second light is blue light. The third light is red light.

Preferably, a substrate, a first light shielding wall, and a second light shielding wall are further included. The substrate has the light emitting unit, the light receiving unit and the controller formed thereon. The first light shielding wall is formed so as to surround the light emitting unit and the light receiving unit along an outer periphery of the substrate. The second light shielding wall partitions space provided by the substrate and the first light shielding wall into space in which the light emitting unit is located and space in which the light receiving unit is located.

Preferably, the information related to the living body is a heart rate.

Preferably, the light emitting unit is a light emitting diode configured to emit white light.

Advantageous Effects of Invention

The living body information sensor according to the present invention is configured to determine, based on the second light included in the reflected light from a living body, whether the living body information sensor is in close contact with the surface of the living body. Based on this determination, the living body information sensor according to the present invention can generate the information about the living body based on the signal with less noise that is obtained when the living body information sensor is in close contact with the surface of the living body, with the result that the accuracy of measurement can be improved.

DESCRIPTION OF EMBODIMENTS

Figure 1:
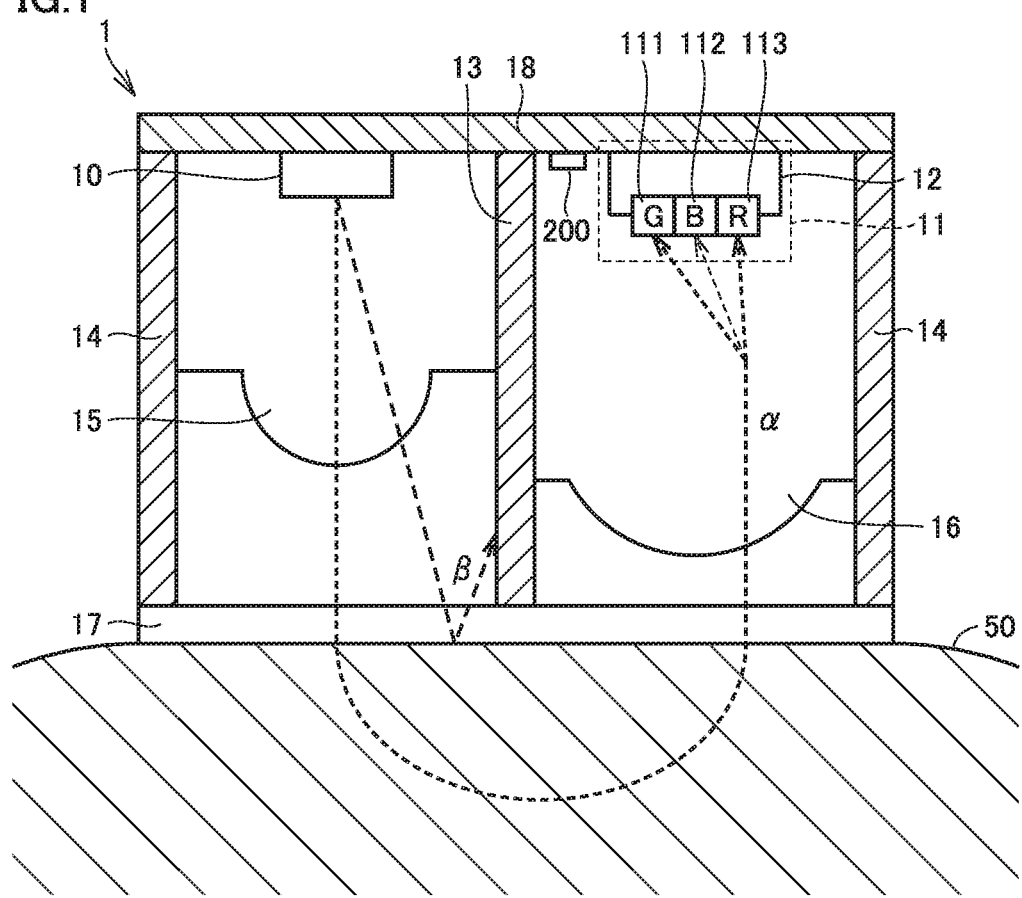
FIG. 1 is a cross-sectional view showing the configuration of a living body information sensor according to the first embodiment.

Embodiments of the present invention will be hereinafter described in detail with reference to the accompanying drawings, in which the same or corresponding components are designated by the same reference characters, and a description thereof will not be repeated.

First Embodiment

FIG. 1 is a cross-sectional view showing the configuration of a living body information sensor 1 according to the first embodiment. In the following, an explanation will be given with regard to the case where living body information sensor 1 measures a heart rate as information about a living body.

Referring to FIG. 1, the living body information sensor includes a light emitting unit 10 provided as a white light-emitting diode (LED), a light receiving unit 11, light shielding walls 13 and 14, lenses 15 and 16, a transparent plate 17, a substrate 18, and a controller 200.

Substrate 18 has a surface on which light emitting unit 10, light receiving unit 11 and controller 200 are formed. Light receiving unit 11 includes a silicon substrate 12, and a G sensor 111, a B sensor 112 and an R sensor 113 that are formed on silicon substrate 12. Controller 200 may be formed on silicon substrate 12.

On the edge of the surface of substrate 18, light shielding wall 14 is formed so as to surround light emitting unit 10 and light receiving unit 11 for preventing external light from entering light receiving unit 11. In the center area on the surface of substrate 18, light shielding wall 13 is formed for preventing white light, which has been emitted from light emitting unit 10, from directly entering light receiving unit 11. In other words, the space provided by light shielding wall 14 is partitioned by light shielding wall 13 into space in which light emitting unit 10 is located and space in which light receiving unit 11 is located.

Lens 15 is provided in the direction in which light emitting unit 10 emits light and lens 16 is provided in the direction in which light receiving unit 11 receives light. Light shielding walls 13 and 14 have lower ends provided with openings that are closed by transparent plate 17. For measuring a heart rate, the surface of transparent plate 17 is brought into close contact with the surface of human body 50.

The white light emitted from light emitting unit 10 is applied through lens 15 and transparent plate 17 to human body 50. Light α included in white light and reflected inside the human body passes through transparent plate 17 and lens 16, and enters light receiving unit 11. G sensor 111 outputs a signal of the level in accordance with the intensity of green light included in light α. B sensor 112 outputs a signal of the level in accordance with the intensity of blue light included in light α. R sensor 113 outputs a signal of the level in accordance with the intensity of red light included in light α. Based on the signal from B sensor 112, controller 200 determines whether living body information sensor 1 is in close contact with the skin surface of human body 50. Also, based on the signal from G sensor 111 and the signal from R sensor 113 that are obtained when living body information sensor 1 is in close contact with the skin surface of human body 50, controller 200 generates a signal showing a heart rate.

As shown in FIG. 1, when living body information sensor 1 is in close contact with human body 50, light β reflected off the skin surface of human body 50 is interrupted by light shielding wall 13, so that this light β hardly enters light receiving unit 11.

Figure 2:
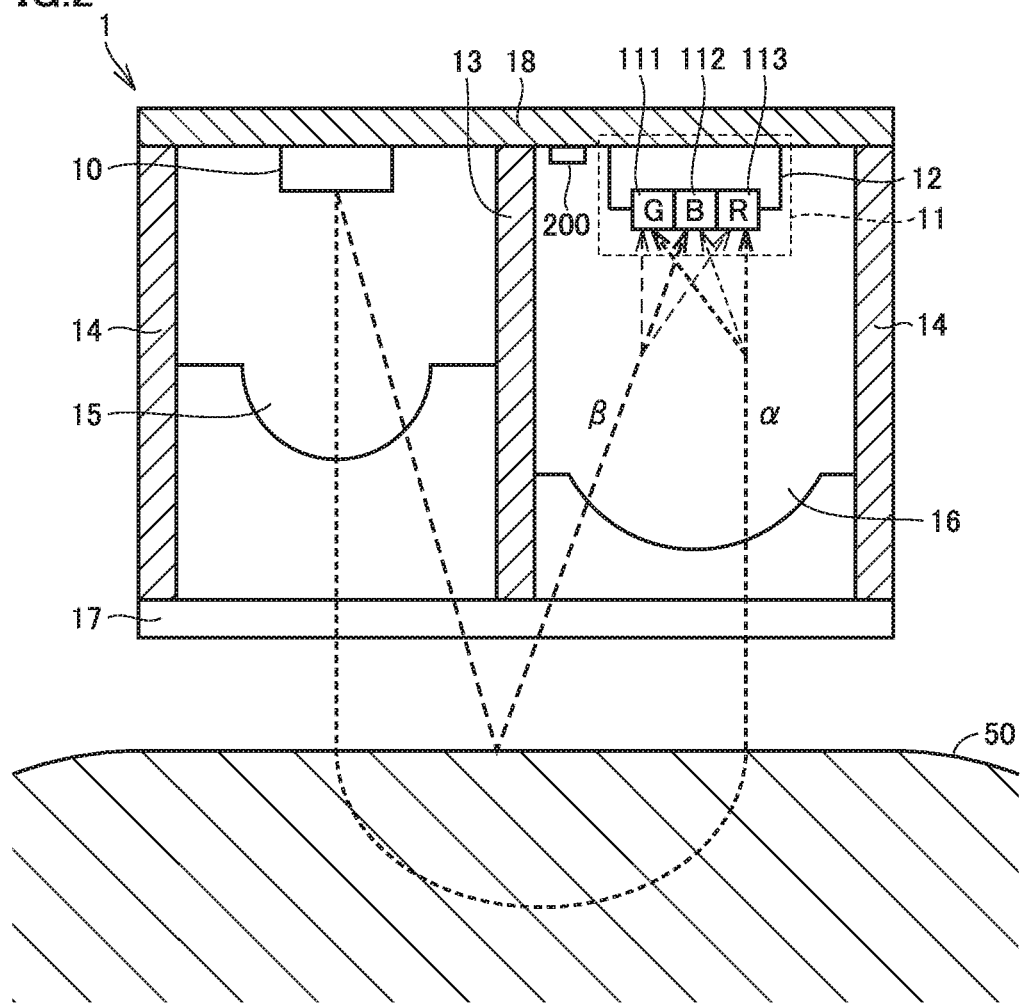
FIG. 2 is a diagram showing the state where the living body information sensor in FIG. 1 is not in close contact with a human body.

On the other hand, when living body information sensor 1 is not in close contact with human body 50 but there is a gap between living body information sensor 1 and the skin surface of human body 50 as shown in FIG. 2, light β enters light receiving unit 11, so that this light β may become a noise when a heart rate is measured.

Thus, in the first embodiment, depending on whether or not the intensity of the blue light entering the light receiving unit is smaller than a prescribed threshold value, it is determined whether or not living body information sensor 1 is in close contact with human body 50. Then, a heart rate is calculated using the signal from G sensor 111 and the signal from R sensor 113 obtained when living body information sensor 1 is in close contact with human body 50.

The blue light emitted to the human body is absorbed inside the human body so that this blue light is hardly reflected inside the human body. Thus, this blue light is hardly included in light α. Since the blue light is reflected mainly off the skin surface, this blue light is included in light β. Accordingly, when living body information sensor 1 is in close contact with human body 50 as shown in FIG. 1, the blue light included in light β is interrupted by light shielding wall 13 so that this blue light hardly enters light receiving unit 11. On the other hand, when living body information sensor 1 is not in close contact with human body 50 but there is a gap between living body information sensor 1 and human body 50 as shown in FIG. 2, the blue light reflected off the skin surface of human body 50 enters light receiving unit 11 through this gap. Thus, by measuring the intensity of the blue light entering light receiving unit 11, it is determined whether living body information sensor 1 is in close contact or not with human body 50.

Figure 3:
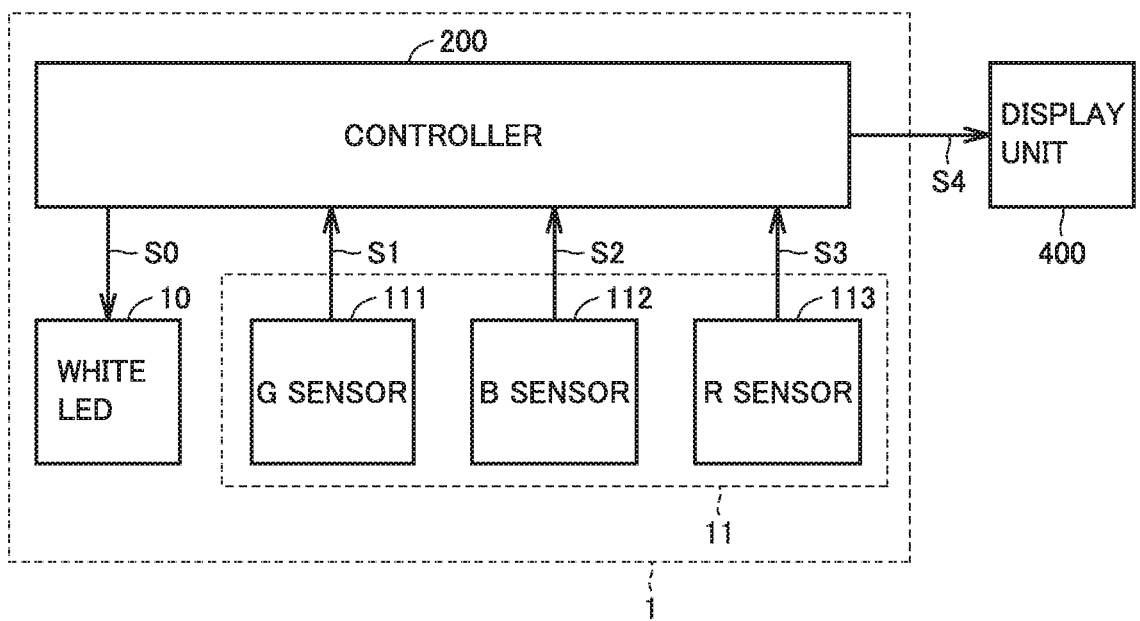
FIG. 3 is a functional block diagram for illustrating the function of the living body information sensor in FIG. 1.

The functional configuration of living body information sensor 1 will be hereinafter described with reference to FIG. 3. Referring to FIG. 3, in response to an instruction from a user to start measurement, controller 200 outputs a control signal S0 to light emitting unit 10. In response to control signal S0 having reached a prescribed level, light emitting unit 10 emits light and outputs white light to a human body. The white light output from light emitting unit 10 is reflected off the human body, and this reflected light enters G sensor 111, B sensor 112 and R sensor 113. Since a part of the white light is absorbed into skin, blood and the like at this time, the intensity of the reflected light changes in accordance with the pulse wave and the body motion of the human body. Specifically, the intensity of the green light included in the reflected light changes in accordance with the pulse wave and the body motion of the human body. The intensity of the red light included in the reflected light changes in accordance with the human body motion, but hardly changes in accordance with pulsation in the human body. The blue light included in the reflected light is mostly reflected off the skin surface, as described above. Thus, this blue light is used for determining whether or not living body information sensor 1 is in close contact with human body 50.

G sensor 111 generates a signal S1 of the level in accordance with the intensity of the incoming green light among each light emitted from light emitting unit 10. The level of signal S1 (for example, a voltage) increases as the intensity of the incoming green light increases. As described above, the level of signal S1 changes in accordance with the pulsation and the motion of the human body.

B sensor 112 generates a signal S2 of the level in accordance with the intensity of the incoming blue light among each light emitted from light emitting unit 10. The level of signal S2 (for example, a voltage) increases as the intensity of the incoming blue light increases.

R sensor 113 receives the light mainly reflected inside the human body among each light emitted from light emitting unit 10, and generates a signal S3 of the level in accordance with the intensity of the red light included in the received light. The level of signal S3 (for example, a voltage) increases as the intensity of the incoming red light increases. As described above, signal S3 changes in accordance with the human body motion, but hardly changes in accordance with the pulsation of the human body.

Controller 200 amplifies at least one of signals S1 and S3 such that the amplitudes of the body motion components of signals S1 and S3 that change in the same period are approximately the same. Controller 200 then calculates a signal showing the level difference between signals S1 and S3. Then, controller 200 generates a signal S4 showing a pulse wave of the human body based on the signal showing the level difference. When the level of signal S2 is less than a prescribed threshold value (when living body information sensor 1 is in close contact with human body 50), controller 200 outputs signal S4 to a display unit 400. Display unit 400 displays characters, images and the like showing a heart rate according to signal S4 from controller 200. Controller 200 and display unit 400 may communicate with each other through wired connection or wirelessly.

Figure 4:
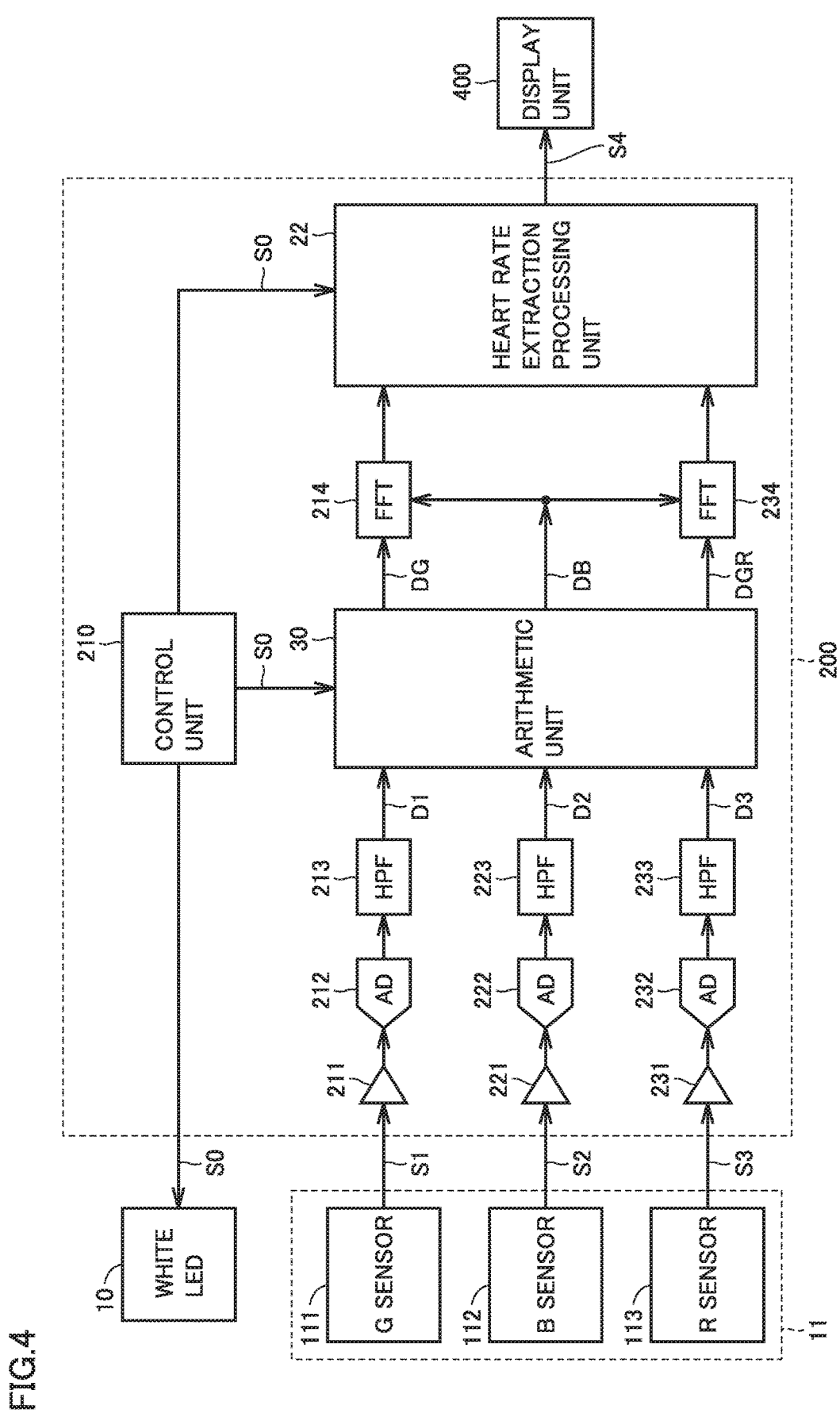
FIG. 4 is a functional block diagram for illustrating the function of a controller in FIG. 3.

The functional configuration of controller 200 will be hereinafter described with reference to FIG. 4. Referring to FIG. 4, controller 200 includes amplifiers 211, 221 and 231, analog-to-digital (AD) converters 212, 222 and 232, high-pass filters (HPF) 213, 223 and 233, an arithmetic unit 30, Fast Fourier Transform (FFT) units 214 and 234, a heart rate extraction processing unit 22, and a control unit 210.

Control unit 210 turns control signal S0 into an "H" level and an "L" level in an alternate manner at a frequency sufficiently higher than the frequency of the pulse wave, to cause light emitting unit 10 to turn on and off in a prescribed period, and also controls the entire controller 200 in synchronization with control signal S0.

G sensor 111 receives the light emitted from light emitting unit 10 and reflected mainly inside the human body, and the light leaked thereinto from the outside in accordance with the body motion. Then, G sensor 111 outputs signal S1 of the level in accordance with the intensity of the green light included in the received light.

B sensor 112 receives the light emitted from light emitting unit 10 and reflected off the skin surface, and the light leaked thereinto from the outside in accordance with the body motion. Then, B sensor 112 outputs signal S2 of the level in accordance with the intensity of the blue light included in the received light.

R sensor 113 receives the light emitted from light emitting unit 10 and reflected inside the human body, and the light leaked thereinto from the outside in accordance with the body motion. Then, R sensor 113 outputs signal S3 of the level in accordance with the intensity of the red light included in the received light.

Amplifier 211 amplifies signal S1 output from G sensor 111. AD converter 212 converts the output signal from amplifier 211 into a digital signal. High-pass filter 213 removes a direct-current (DC) component in the output signal of AD converter 212. The signal having passed through high-pass filter 213 is output to arithmetic unit 30 as a digital signal D1.

Amplifier 221 amplifies signal S2 output from B sensor 112. AD converter 222 converts the output signal from amplifier 221 into a digital signal. High-pass filter 223 removes a DC component in the output signal of AD converter 222. The signal having passed through high-pass filter 223 is output to arithmetic unit 30 as a digital signal D2.

Amplifier 231 amplifies signal S3 output from R sensor 113. AD converter 232 converts the output signal from amplifier 231 into a digital signal. High-pass filter 233 removes a DC component in the output signal of AD converter 232. The signal having passed through high-pass filter 233 is output to arithmetic unit 30 as a digital signal D3.

Figure 5:
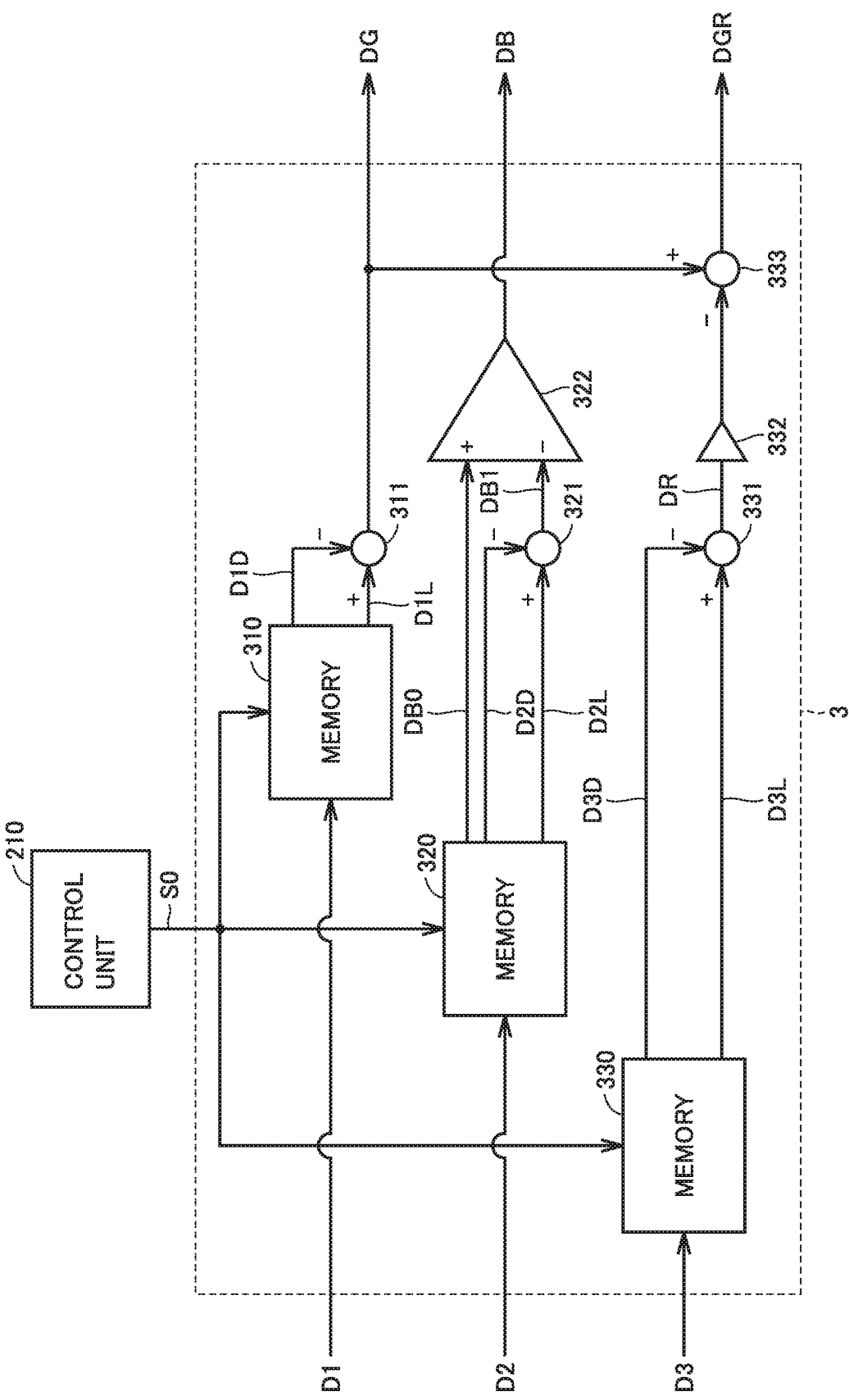
FIG. 5 is a functional block diagram for illustrating the details of an arithmetic unit in FIG. 4.

Arithmetic unit 30 includes memories 310, 320 and 330, subtracters 311, 321, 331, and 333, and an amplifier 332, as shown in FIG. 5.

Memory 310 temporarily stores digital signal D1 as a digital signal D1D in a time frame during which control signal S0 is at an "L" level (that is, the time frame during which light emitting unit 10 is turned off), and temporarily stores digital signal D1 as a digital signal D1L in a time frame during which control signal S0 is at an "H" level (that is, the time frame during which light emitting unit 10 is turned on). After that, memory 310 outputs digital signals D1D and D1L to subtracter 311.

Digital signal D1D includes a noise component resulting from the light and the like having leaked into G sensor 111 from the outside in the time frame during which light emitting unit 10 is turned off. This noise component is included also in digital signal D1L. Subtracter 311 subtracts digital signal D1D from digital signal D1L, and outputs a digital signal DG. Therefore, digital signal DG is provided as a signal obtained by removing a noise component from digital signal D1L.

Memory 320 temporarily stores digital signal D2 as a digital signal D2D in a time frame during which control signal S0 is at an "L" level (that is, the time frame during which light emitting unit 10 is turned off), and also temporarily stores digital signal D2 as a digital signal D2L in a time frame during which control signal S0 is at an "H" level (that is, the time frame during which light emitting unit 10 is turned on). After that, memory 320 outputs digital signals D2D and D2L to subtracter 321.

Digital signal D2D includes a noise component resulting from the light and the like having leaked into B sensor 112 from the outside in the time frame during which light emitting unit 10 is turned off. This noise component is included also in digital signal D2L. Subtracter 321 subtracts digital signal D2D from digital signal D2L, and outputs digital signal DB1 to comparator 322. Accordingly, digital signal DB1 is provided as a signal obtained by removing a noise component from digital signal D2L.

Memory 320 stores a prescribed threshold value used for determining whether living body information sensor 1 is in contact or not with human body 50, and outputs a digital signal DB0 of the level showing this threshold value to comparator 322.

Comparator 322 compares the level of digital signal DB0 with the level of digital signal DB1. When the level of digital signal DB1 is less than the level of digital signal DB0 (when living body information sensor 1 is in close contact with human body 50), comparator 322 outputs the level of digital signal DB as "H". When the level of digital signal DB1 is equal to or greater than the level of digital signal DB0 (when living body information sensor 1 is not in close contact with human body 50), comparator 322 outputs the level of digital signal DB as "L".

Memory 330 temporarily stores digital signal D3 as a digital signal D3D in a time frame during which control signal S0 is at an "L" level (that is, the time frame during which light emitting unit 10 is turned off), and temporarily stores digital signal D3 as a digital signal D3L in a time frame during which control signal S0 is at an "H" level (that is, the time frame during which light emitting unit 10 is turned on). After that, memory 330 outputs digital signals D3D and D3L to subtracter 331.

Digital signal D3D includes a noise component resulting from the light and the like having leaked into R sensor 113 from the outside in the time frame during which light emitting unit 10 is turned off. This noise component is included also in digital signal D3L. Subtracter 331 subtracts digital signal D3D from digital signal D3L, and outputs a digital signal DR. Therefore, digital signal DR is provided as a signal obtained by removing a noise component from digital signal D3L.

Digital signal DG mainly includes a body motion component and a pulse wave component. Digital signal DR mainly includes a body motion component. Amplifier 332 amplifies digital signal DR such that the level of the body motion component included in digital signal DG and the level of the body motion component included in digital signal DR are almost the same. Subtracter 333 subtracts digital signal DR from digital signal DG, and outputs a digital signal DGR. Digital signal DGR is a signal obtained by subtracting digital signal DR including a body motion component from digital signal DG including a body motion component and a pulse wave component. Accordingly, it can be said that this digital signal DGR mainly includes a pulse wave component.

In addition, although digital signal DR is amplified by amplifier 332 in arithmetic unit 30 shown in FIG. 5, the present invention is not limited thereto, but at least one of digital signals DG and DR may be amplified or attenuated such that the levels of the body motion components included in digital signals DG and DR are almost the same.

Again referring to FIG. 4, when the level of digital signal DB is at "H" (when living body information sensor 1 is in close contact with human body 50), FFT unit 214 applies fast Fourier transform to digital signal DG to generate a frequency spectrum of digital signal DG, and outputs the generated frequency spectrum to heart rate extraction processing unit 22. When the level of digital signal DB is at "L" (when living body information sensor 1 is not in close contact with human body 50), FFT unit 214 does not output the generated frequency spectrum.

When the level of digital signal DB is at "H", FFT unit 234 applies fast Fourier transform to digital signal DGR to generate a frequency spectrum of digital signal DGR, and outputs the generated frequency spectrum to heart rate extraction processing unit 22. When the level of digital signal DB is at "L", FFT unit 234 does not output the generated frequency spectrum.

Heart rate extraction processing unit 22 calculates the heart rate of a human body based on the frequency spectra output from FFT units 214 and 234, and outputs a signal S4 showing the calculated heart rate to display unit 400.

Figure 6:
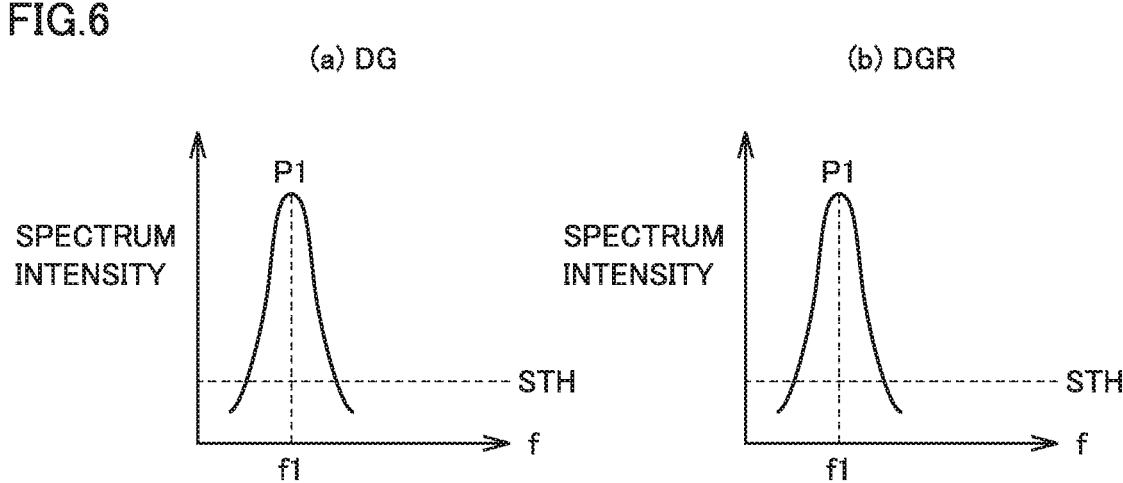
FIG. 6 is a frequency spectrum diagram showing the operation of a heart rate extraction processing unit when the body motion is relatively small.
Figure 7:
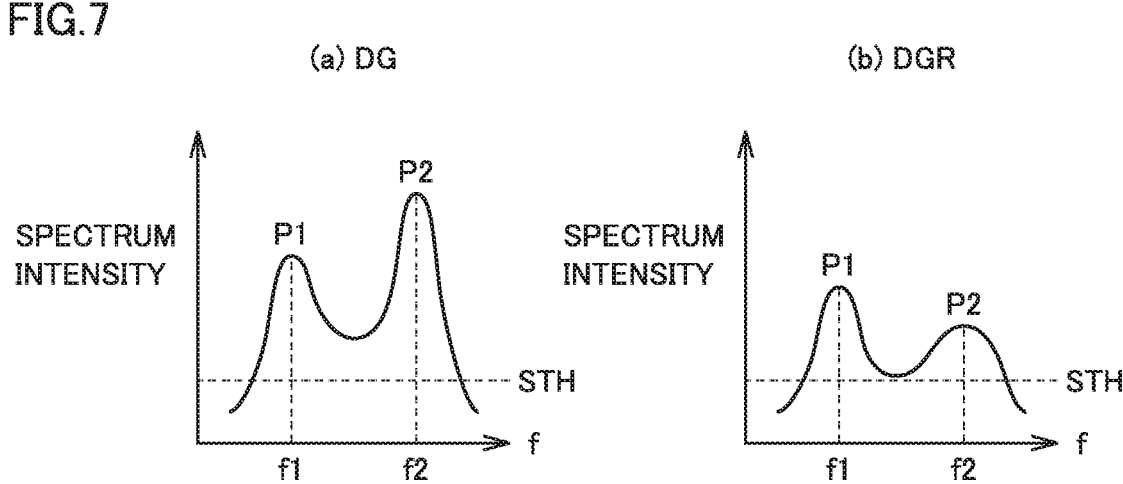
FIG. 7 is a frequency spectrum diagram showing the operation of the heart rate extraction processing unit when the body motion is not negligible.

The operation of heart rate extraction processing unit 22 will be hereinafter described with reference to FIGS. 6 and 7. FIGS. 6(a) and 7(a) each show a frequency spectrum of digital signal DG generated in FFT unit 214 (see FIG. 4). FIGS. 6(b) and 7(b) each show a frequency spectrum of digital signal DGR generated in FFT unit 234 (see FIG. 4). The frequency of the peak at which the spectrum intensity falls within a range equal to or greater than a predetermined threshold value STH is defined as a candidate for the pulse wave frequency.

When the human body motion is relatively small (for example, when the user remains stationary), digital signal DG hardly includes a body motion component. In other words, digital signal DG and digital signal DGR are almost the same signal. Thus, the frequency spectra of digital signals DG and DGR have the same shape formed in a curved line including one peak P1 protruding upward, as shown in FIGS. 6(a) and 6(b). In this case, heart rate extraction processing unit 22 determines a frequency f1 of peak P1 as a frequency of the pulse wave. Then, heart rate extraction processing unit 22 calculates the heart rate [times/minute] based on this frequency f1, and outputs signal S4 showing this heart rate [times/minute] to display unit 400.

When the human body motion is not negligible (for example, when the user is jogging), the frequency spectra of digital signals DG and DGR each show a curved line including two peaks P1 and P2 each protruding upward, as shown in FIGS. 7(a) and 7(b). As described above, digital signal DG mainly includes a body motion component and a pulse wave component while digital signal DGR mainly includes a pulse wave component. In other words, it can be said that digital signal DGR is less in body motion component than digital signal DG. Thus, heart rate extraction processing unit 22 calculates a rate at which the heights of peaks P1 and P2 of the frequency spectrum of digital signal DGR decreases with respect to the heights of peaks P1 and P2 of the frequency spectrum of digital signal DG (the decrease rate). Heart rate extraction processing unit 22 determines a frequency f2 of the peak with the higher decrease rate (in this case, P2) as a frequency of the body motion, and determines frequency f1 of the peak with the lower decrease rate (in this case, P1) as a frequency of the pulse wave. Then, heart rate extraction processing unit 22 calculates a heart rate [times/minute] based on this frequency f1, and outputs signal S4 showing the heart rate [times/minute] to display unit 400.

As described above, according to living body information sensor 1, it is determined based on the intensity of the blue light reflected off the skin surface of human body 50 whether or not living body information sensor 1 is in close contact with the surface of human body 50. Thereby, a heart rate can be calculated based on the signal with less noise obtained when living body information sensor 1 is in close contact with human body 50. As a result, the accuracy of measurement can be improved.

[Confirmation Experiment in the First Embodiment]

In the first embodiment, it is determined based on the blue light entering light receiving unit 11 whether or not living body information sensor 1 is in close contact with human body 50. The inventors of the present application have conducted an experiment in which the blue light entering light receiving unit 11 is intentionally adjusted so as to pseudo-reproduce the situation where living body information sensor 1 is not in close contact with human body 50, thereby confirming that it can be determined based on the blue light entering light receiving unit 11 whether or not living body information sensor 1 is in close contact with human body 50. This confirmation experiment will be hereinafter described.

Figure 8:
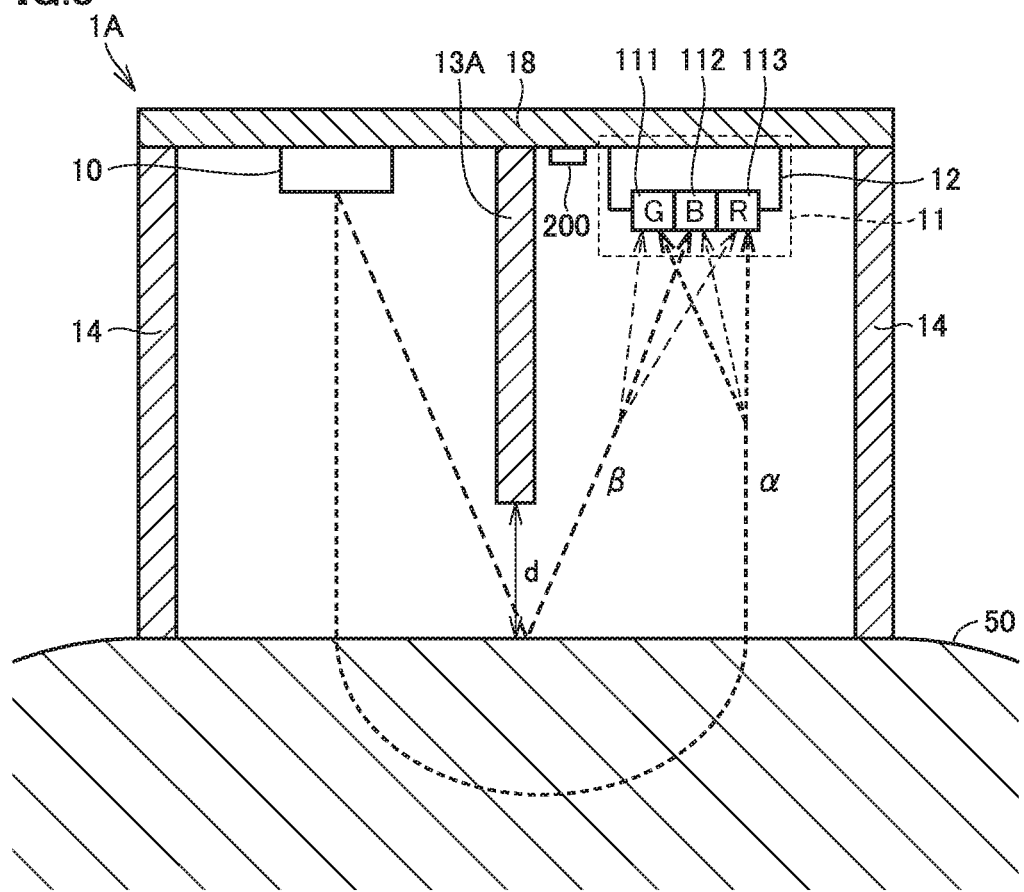
FIG. 8 is a cross-sectional view showing the configuration of the living body information sensor used in a confirmation experiment in the first embodiment.

FIG. 8 is a cross-sectional view showing the configuration of a living body information sensor 1A used in a confirmation experiment in the first embodiment. Living body information sensor 1A is different from living body information sensor 1 in that living body information sensor 1A does not include a transparent plate, and that there is variability in the distance between the end of the light shielding wall and the skin surface of the human body in the state where living body information sensor 1A is attached to the human body. Since other configurations of living body information sensor 1A are similar to those of living body information sensor 1, the description of the similar configurations will not be repeated.

Referring to FIG. 8, living body information sensor 1A includes a light shielding wall 13A. There is variability in the distance between the end of light shielding wall 13A on the human body 50 side and the skin surface of human body 50 in the state where living body information sensor 1A is attached to human body 50 (which will be hereinafter also referred to as a "raised distance d").

When living body information sensor 1A is attached to human body 50, the light reflected off the skin surface of human body 50 among each light emitted from light emitting unit 10 is less likely to enter light receiving unit 11 as raised distance d is smaller. In contrast, this light reflected off the skin surface of human body 50 is more likely to enter light receiving unit 11 as raised distance d is larger. In other words, the case where raised distance d is relatively small in living body information sensor 1A corresponds to the case where living body information sensor 1 according to the first embodiment is in close contact with the human body. On the other hand, the case where raised distance d is relatively large in living body information sensor 1A corresponds to the case where living body information sensor 1 is not in close contact with the human body.

Figure 9:
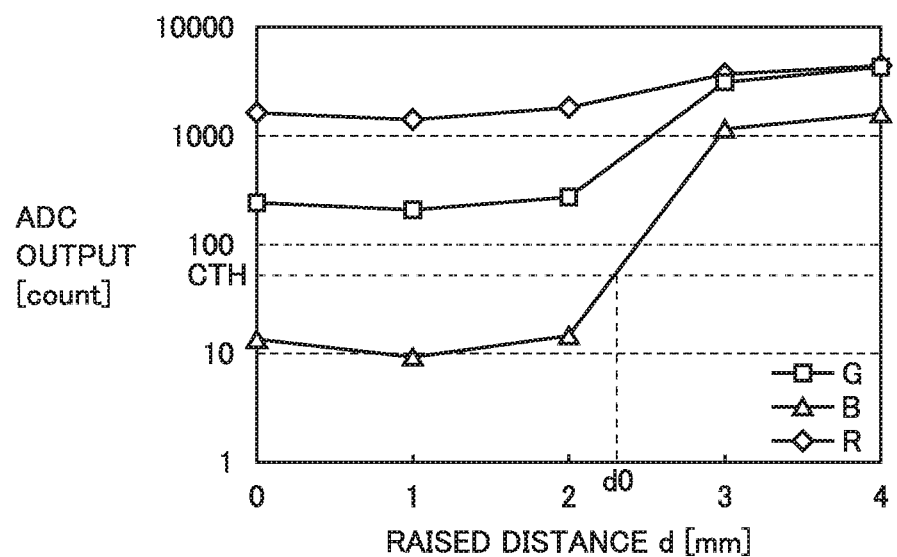
FIG. 9 is a diagram showing the relation between a raised distance and each of the intensity of green light, the intensity of red light and the intensity of blue light that enter a light receiving unit.

FIG. 9 is a diagram showing the relation between raised distance d and each of the intensity of green light, the intensity of red light and the intensity of blue light that enter light receiving unit 11. As the intensity of each light entering light receiving unit 11 is larger, the output (ADC count) of the AD converter (see FIG. 4) for converting the signal output from light receiving unit 11 into a digital signal becomes larger. Accordingly, FIG. 9 shows the relation between raised distance d and the intensity of each light as the relation between raised distance d and the ADC count corresponding to each light. FIG. 9 shows a plot of the ADC count corresponding to each of lights obtained in the case where raised distances are 1 mm, 2 mm, 3 mm, and 4 mm. These points are connected by a straight line. A plot point G shows the relation between raised distance d and the ADC count corresponding to the green light entering light receiving unit 11. A plot point B shows the relation between raised distance d and the ADC count corresponding to the blue light. A plot point R shows the relation between raised distance d and the ADC count corresponding to the red light.

Referring to FIG. 9, when raised distance d is 0 mm to 2 mm, the intensity of the green light, the intensity of the blue light and the intensity of the red light that enter light receiving unit 11 hardly change. On the other hand, when raised distance d is 3 mm, the intensity of the blue light entering light receiving unit 11 is remarkably increased as compared with the intensity of the green light and the intensity of the red light. When raised distance d is 4 mm, the intensity of each light is hardly different from that in the case where raised distance d is 3 mm.

When living body information sensor 1 according to the first embodiment and human body 50 are not in close contact with each other, and when a gap occurs between living body information sensor 1 and human body 50, the blue light interrupted by the light shielding wall while living body information sensor 1 and human body 50 are in close contact with each other is caused to enter light receiving unit 11 through the gap. Accordingly, the blue light entering light receiving unit 11 must suddenly increase. In FIG. 9, the intensity of the blue light entering light receiving unit 11 is suddenly increased while raised distance d changes from 2 mm to 3 mm. Thus, assuming that CTH as an ADC count corresponding to raised distance d0 (2<d0<3) is defined as a threshold value, the case where the ADC count of the blue light is equal to or greater than threshold value CTH is regarded as the case where living body information sensor 1 is not in close contact with human body 50.

Figure 10:
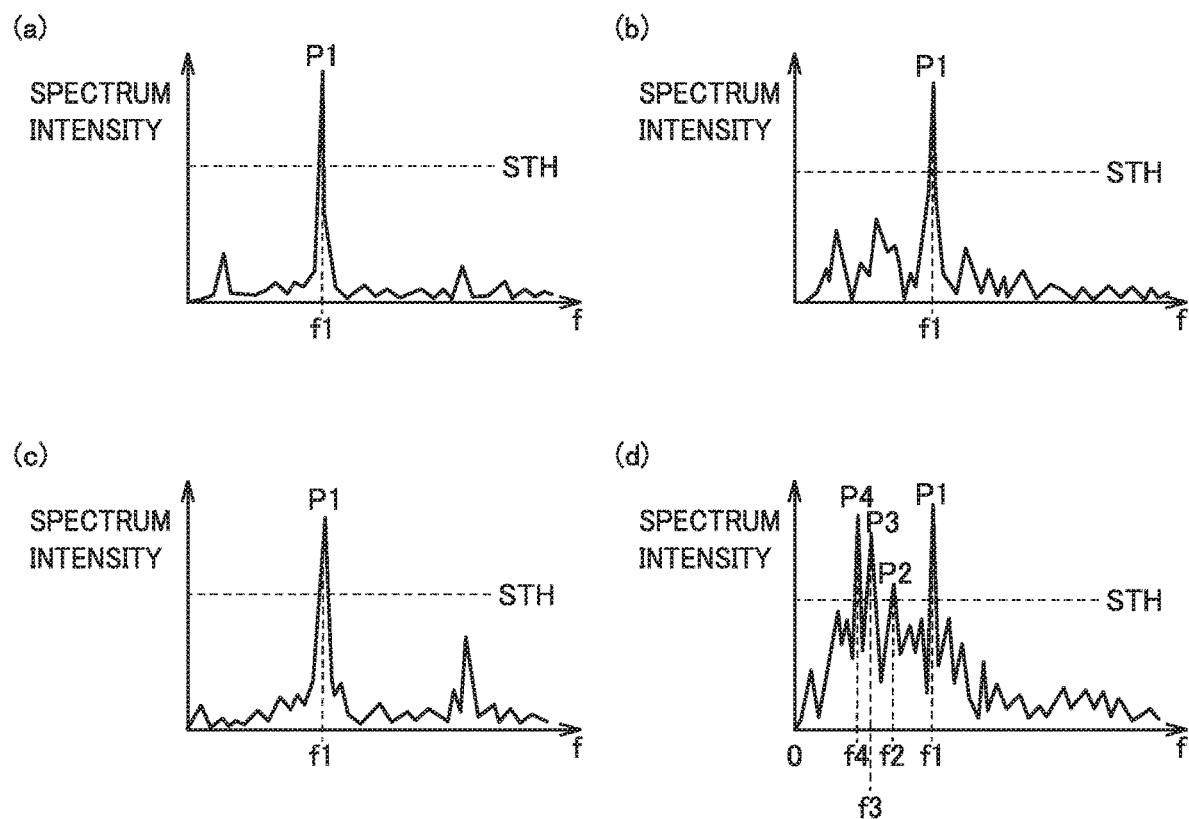
FIG. 10 is a diagram showing a frequency spectrum generated by an FFT unit in FIG. 4.

FIG. 10 is a diagram showing a frequency spectrum generated by FFT unit 214 or FFT unit 234 (see FIG. 4). FIGS. 10(a), 10(b), 10(c), and 10(d) show the cases where raised distances are 0 mm, 1 mm, 2 mm, and 3 mm, respectively. Also in FIG. 10, the frequency of the peak at which the spectral intensity exists in the range equal to or greater than predetermined threshold value STH as in FIG. 7 is defined as a candidate for the frequency of the pulse wave.

FIGS. 10(a), 10(b), 10(c), and 10(d) each show data obtained in the case where living body information sensor 1A is attached to non-moving human body 50. Accordingly, these pieces of data hardly include body motion components, but mainly include pulse wave components. Thus, the frequency spectra generated by FFT unit 214 and FFT unit 234 are to have almost the same shape while the peak existing in the range equal to or greater than threshold value STH is to include only a pulse wave component.

Referring to FIGS. 10(a), 10(b) and 10(c), each peak existing in the range equal to or greater than threshold value STH is only peak P1. Accordingly, frequency f1 is defined as a frequency of the pulse wave. On the other hand, referring to FIG. 10(d), the peaks existing in the range equal to or greater than threshold value STH are defined as peaks P1, P2, P3, and P4. Accordingly, it cannot be specified as to which one of frequencies f1, f2, f3, and f4 corresponding to peaks P1, P2, P3, and P4, respectively, is defined as a frequency of the pulse wave. Thus, a heart rate cannot be extracted from FIG. 10(d).

From the above description, the frequency spectra shown in FIGS. 10(a), 10(b) and 10(c) may be recognized as corresponding to the frequency spectra generated based on the data with less noise that is obtained when living body information sensor 1 is in close contact with human body 50, and thus, may be recognized as data that should be used in extracting a heart rate. On the other hand, the frequency spectrum in FIG. 10(d) may be recognized as corresponding to the frequency spectrum generated based on the data including, as a noise, the light reflected off the skin surface of the human body in the state where living body information sensor 1 is not in close contact with human body 50, and thus, may be recognized as data that should not be used in extracting a heart rate.

Referring to FIGS. 9 and 10, the ADC count of the blue light becomes less than threshold value CTH when the raised distances are 0 mm, 1 mm, and 2 mm, which correspond to FIGS. 10(a), 10(b), and 10(c), respectively. The ADC count of the blue light becomes equal to or greater than threshold value CTH when raised distance becomes equal to or greater then d0, which corresponds to FIG. 10(d). Accordingly, if the case where the ADC count of the blue light becomes equal to or greater than threshold value CTH is regarded as the case where living body information sensor 1 is not in close contact with human body 50, a heart rate can be calculated based on the data with less noise obtained when living body information sensor 1 is in close contact with human body 50. Consequently, the accuracy of measurement by living body information sensor 1 can be improved.

Second Embodiment

Figure 11:
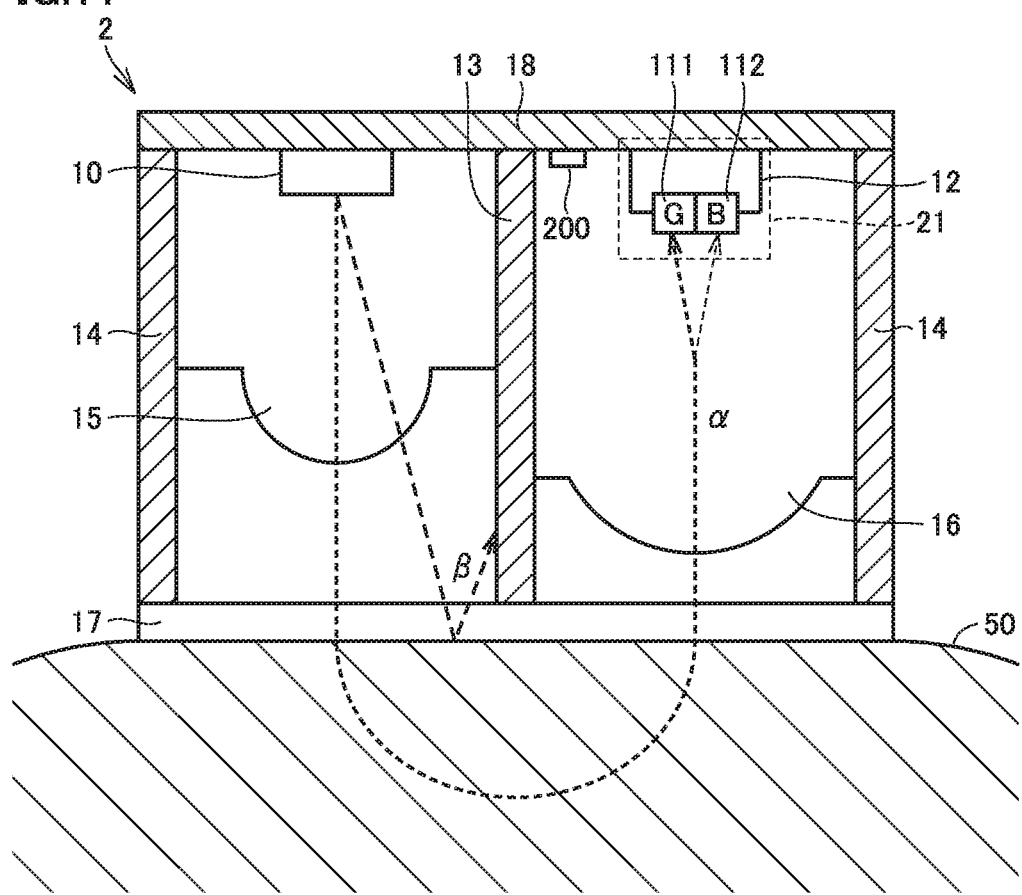
FIG. 11 is a cross-sectional view showing the configuration of a living body information sensor according to the second embodiment.

In the first embodiment, a heart rate is measured using the G sensor, the B sensor, and the R sensor. The heart rate can be measured using the G sensor and the B sensor even without using the R sensor. Like living body information sensor 2 shown in FIG. 11, the living body information sensor according to the present embodiment may be configured such that light receiving unit 21 does not include an R sensor and a heart rate is measured by G sensor 111 and B sensor 112.

Also by living body information sensor 2, based on the intensity of the blue light reflected off the skin surface of the human body and entering light receiving unit 21, it is determined whether living body information sensor 2 is in close contact with the surface of human body 50. Thereby, a heart rate can be calculated based on the signal with less noise obtained when living body information sensor 2 is in close contact with human body 50. Consequently, the accuracy of measurement can be improved.

In living body information sensor 2, light receiving unit 21 does not include an R sensor. Thus, living body information sensor 2 is slightly inferior in heart-rate measuring accuracy as compared with living body information sensor 1. However, as compared with living body information sensor 1, the cost of manufacturing living body information sensor 2 can be reduced since living body information sensor 2 does not require an R sensor. Accordingly, living body information sensor 2 may be selected as appropriate from the viewpoint of the balance between the required accuracy of measurement and the manufacturing cost.

In the above-described embodiments, although a heart rate is measured as information about a living body, the information about a living body is not limited to a heart rate, but may be for example an oxygen saturation concentration in blood.

In the above-described embodiments, light emitting unit 10 emitting white light is used, but a green LED emitting green light and a blue LED emitting blue light may be provided in place of light emitting unit 10, and also, a red LED emitting red light may be provided as required.

The living body information sensor according to each of the above-described embodiments allows detection of a heart rate not only of a human body but also of living bodies including humans and animals.

It should be understood that the embodiments disclosed herein are illustrative and non-restrictive in every respect. The scope of the present invention is defined by the terms of the claims, rather than the description above, and is intended to include any modifications within the meaning and scope equivalent to the terms of the claims.

REFERENCE SIGNS LIST 1, 1A, 2 living body information sensor, 10 light emitting unit, 11, 21 light receiving unit, 12 silicon substrate, 13, 13A, 14 light shielding wall, 15, 16 lens, 17 transparent plate, 18 substrate, 22 heart rate extraction processing unit, 30 arithmetic unit, 50 human body, 111, 112, 113 sensor, 200 controller, 210 control unit, 211, 221, 231, 332 amplifier, 212, 222, 232 AD converter, 213, 223, 233 high-pass filter, 214, 234 FET unit, 310, 320, 330 memory, 311, 321, 331, 333 subtracter, 322 comparator, 400 display unit, B, G, R plot point, CTH, STH threshold value, D1L, D1, D1D, D2D, D2L, D2, D3L, D3, D3D, DB, DB0, DB1, DG, DGR, DR digital signal, P1, P2, P3, P4 peak, S0 control signal, S1, S2, S3, S4 signal, T1 period, d, d0 raised distance, f1, f2, f3, f4 frequency.

The invention claimed is:

1. A living body information sensor configured to be attached to a living body and to generate information related to the living body, the living body information sensor comprising:
  a light emitting unit configured to emit light including first light and second light;
  a light receiving unit including a first optical sensor and a second optical sensor, the light receiving unit being configured to output a signal of a level in accordance with intensity of incoming light; and
  a controller configured to receive the signal output from the light receiving unit to generate the information related to the living body,
  the second light being blue light,
  the living body information sensor being configured such that when the living body information sensor is attached to the living body, light emitted from the light emitting unit being reflected off the living body and entering the light receiving unit,
  the first optical sensor being configured to output a first signal of a level in accordance with intensity of the first light entering the light receiving unit, the second optical sensor being configured to output a second signal of a level in accordance with intensity of the second light entering the light receiving unit, and the controller being configured to:
determine, based on the second signal, whether or not the living body information sensor and a surface of the living body are in close contact with each other; and generate the information related to the living body based on the first signal obtained when the living body information sensor and the surface of the living body are in close contact with each other, wherein, when the level of the second signal is smaller than a prescribed threshold value, the controller determines that the living body information sensor and the surface of the living body are in close contact with each other, wherein:
the light emitted from the light emitting unit further includes third light, the light receiving unit further includes a third optical sensor configured to output a third signal of a level in accordance with intensity of the third light entering the light receiving unit, and the controller is configured to generate the information related to the living body based on the first signal and the third signal that are obtained when the living body information sensor and the surface of the living body are in close contact with each other, wherein:
each of the first signal and the third signal includes a body motion component, and the controller is configured to:
amplify or attenuate at least one of the first signal and the third signal such that the amplitudes of the body motion components of the first signal and the third signal that change in the same period are approximately the same; and calculate a fourth signal showing a level difference between the first signal and the third signal.

2. The living body information sensor according to claim 1, wherein the controller is configured to generate the information related to the living body based on a difference between the level of the first signal and the level of the third signal.

3. The living body information sensor according to claim 1, wherein
the first light is green light, and
the third light is red light.

4. The living body information sensor according to claim 1, further comprising:
a substrate on which the light emitting unit, the light receiving unit and the controller are formed;
a first light shielding wall formed so as to surround the light emitting unit and the light receiving unit along an outer periphery of the substrate; and
a second light shielding wall partitioning space provided by the substrate and the first light shielding wall into space in which the light emitting unit is located and space in which the light receiving unit is located.

5. The living body information sensor according to claim 1, wherein the information related to the living body is a heart rate.

6. The living body information sensor according to claim 1, wherein the light emitting unit is a light emitting diode configured to emit white light.

7. The living body information sensor according to claim 1, further comprising:
a first lens provided in a direction in which the light emitting unit emits light; and
a second lens provided in a direction in which the light receiving unit receives light,
wherein a distance between the light emitting unit and the first lens is shorter than a distance between the light receiving unit and the second lens.

8. A living body information sensor configured to be attached to a living body and to generate information related to the living body, the living body information sensor comprising:
a light emitting unit configured to emit light including first light and second light;
a light receiving unit including a first optical sensor and a second optical sensor, the light receiving unit being configured to output a signal of a level in accordance with intensity of incoming light; and
a controller configured to receive the signal output from the light receiving unit to generate the information related to the living body,
the second light being blue light,
the living body information sensor being configured such that when the living body information sensor is attached to the living body, light emitted from the light emitting unit being reflected off the living body and entering the light receiving unit,
the first optical sensor being configured to output a first signal of a level in accordance with intensity of the first light entering the light receiving unit,
the second optical sensor being configured to output a second signal of a level in accordance with intensity of the second light entering the light receiving unit, and
the controller being configured to:
determine, based on the second signal, whether or not the living body information sensor and a surface of the living body are in close contact with each other; and
generate the information related to the living body based on the first signal obtained when the living body information sensor and the surface of the living body are in close contact with each other,
wherein, when the level of the second signal is smaller than a prescribed threshold value, the controller determines that the living body information sensor and the surface of the living body are in close contact with each other, and
wherein the controller is configured to cause the light emitting unit to alternately turn on and off at a frequency higher than a frequency of a pulse wave of the living body.

9. The living body information sensor according to claim 8, wherein the controller is configured to:
subtract a first digital signal from a second digital signal to obtain a third digital signal, the first digital signal corresponding to the first signal in a time frame during which the light emitting unit is turned off, the second digital signal corresponding to the first signal in a time frame during which the light emitting unit is turned on, and
apply fast Fourier transform to the third digital signal to generate a frequency spectrum of the third digital signal.

10. The living body information sensor according to claim 8, further comprising:

a substrate on which the light emitting unit, the light receiving unit and the controller are formed;

a first light shielding wall formed so as to surround the light emitting unit and the light receiving unit along an outer periphery of the substrate; and a second light shielding wall partitioning space provided by the substrate and the first light shielding wall into space in which the light emitting unit is located and space in which the light receiving unit is located.

11. The living body information sensor according to claim 8, wherein the information related to the living body is a heart rate.

12. The living body information sensor according to claim 8, wherein the light emitting unit is a light emitting diode configured to emit white light.

13. The living body information sensor according to claim 8, further comprising:

a first lens provided in a direction in which the light emitting unit emits light; and a second lens provided in a direction in which the light receiving unit receives light, wherein a distance between the light emitting unit and the first lens is shorter than a distance between the light receiving unit and the second lens.

* * * * *